United States Patent [19]

Heitzmann

[11] Patent Number: 4,557,900
[45] Date of Patent: Dec. 10, 1985

[54] OPTICAL SENSOR WITH BEADS

[75] Inventor: Harold A. Heitzmann, Costa Mesa, Calif.

[73] Assignee: Cardiovascular Devices, Inc., Irvine, Calif.

[21] Appl. No.: 425,420

[22] Filed: Sep. 28, 1982

[51] Int. Cl.[4] ............... G01N 21/77; G01N 21/78; G01N 33/52

[52] U.S. Cl. .................................. 422/55; 422/56; 422/87; 422/91

[58] Field of Search ............ 422/55, 56, 58, 86, 422/87, 91; 436/68, 165, 167, 168, 169, 170, 178, 127, 133, 136, 172

[56] References Cited

U.S. PATENT DOCUMENTS

| | | | |
|---|---|---|---|
| 3,418,083 | 10/1968 | Rey et al. | 436/170 X |
| 3,616,251 | 10/1971 | Lecco et al. | 435/805 X |
| 3,824,150 | 7/1974 | Lilly et al. | 435/179 X |
| 3,993,451 | 11/1976 | Verbeck | 422/58 X |
| 4,003,707 | 1/1977 | Lübbers et al. | 436/68 X |
| 4,102,746 | 7/1978 | Goldberg | 435/288 X |
| 4,200,110 | 4/1980 | Peterson et al. | |
| 4,356,149 | 10/1982 | Kitajima et al. | 422/56 X |
| 4,438,067 | 3/1984 | Siddiqi | 422/56 |

Primary Examiner—Arnold Turk
Assistant Examiner—Robert J. Hill, Jr.
Attorney, Agent, or Firm—Gordon L. Peterson

[57] ABSTRACT

An optical sensor comprising a selectively permeable matrix of hydrophobic material and a plurality of hydrophilic beads dispersed in the matrix. At least some of the beads carry an optical indicator. The matrix is capable of transmitting light at least at selected wavelengths from outside the matrix to the beads.

21 Claims, 4 Drawing Figures

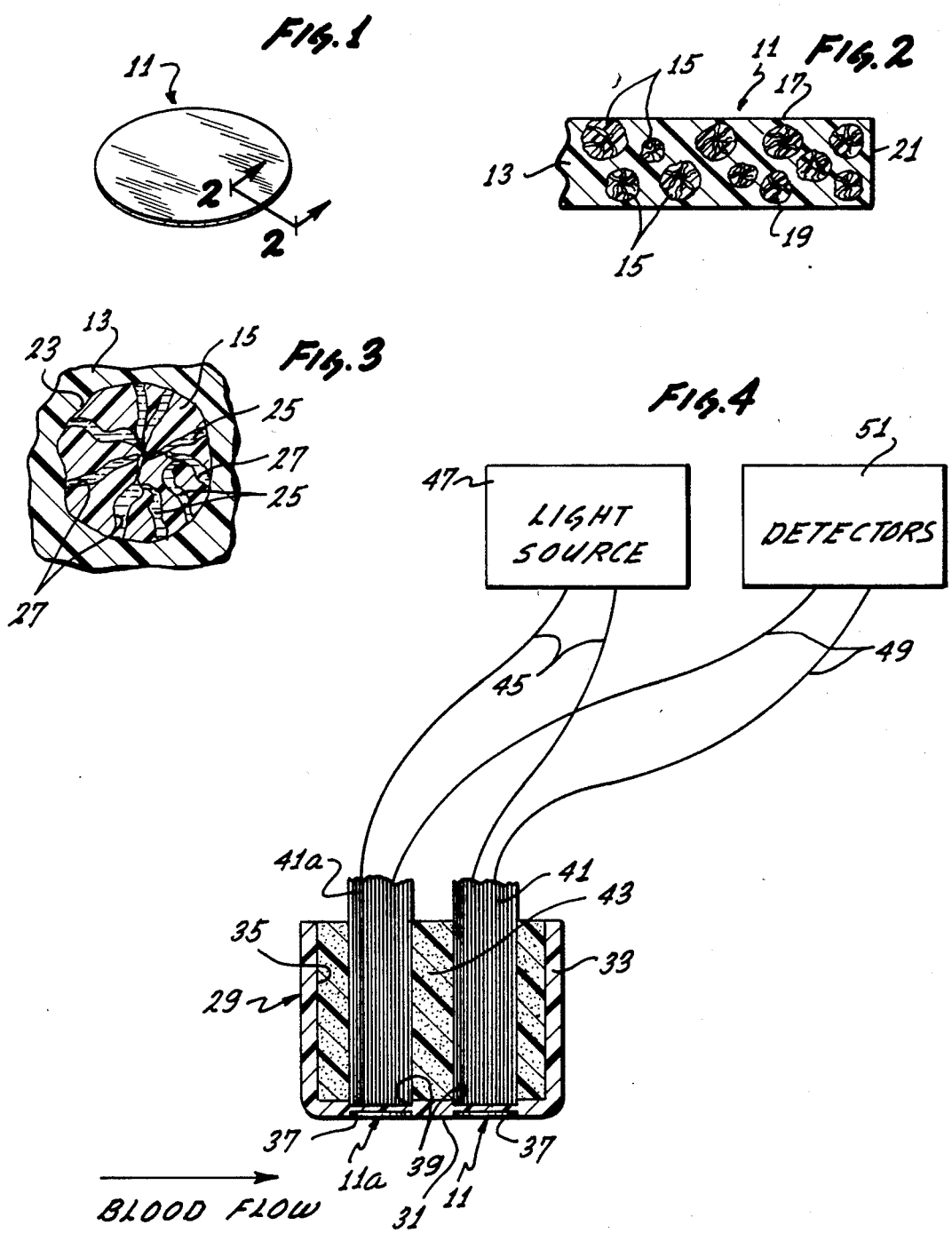

OPTICAL SENSOR WITH BEADS

BACKGROUND OF THE INVENTION

In analyzing samples containing gases, it is often necessary or desirable to ascertain the partial pressure of various gases contained within the sample. A common example is determining the partial pressures of gases in blood, such as carbon dioxide and oxygen. In addition, pH value, the concentration of certain ions and temperature of the blood may need to be determined.

One prior art technique for determining the partial pressure of carbon dioxide employs an electrode with an indicator layer sandwiched between the electrode and a semi-permeable membrane. When the membrane is placed in contact with the blood, the membrane transmits the carbon dioxide to the indicator and essentially excludes the liquid component of the blood. The indicator, which is retained in a nylon mesh, responds to the carbon dioxide, and this response can be measured electrically to provide an indication of the partial pressure of carbon dioxide in the blood.

An optical technique for measuring the partial pressure of blood gases is disclosed in Lubbers et al U.S. Pat. No. 4,003,707. The Lubbers patent discloses an optode which comprises an indicator confined between a semi-permeable membrane and a light-transmitting member of glass or other material. Light is directed through the light-transmitting member to the indicator, and the indicator provides a fluorescent output signal. The membrane transmits the gas of interest, and the indicator responds to the partial pressure of such gas to vary the output signal.

The optical technique disclosed in the Lubbers et al patent has the advantage of avoiding the electrical apparatus necessary for utilizing the electrode type sensor. However, Lubbers et al's optode in the form shown in the patent would be difficult and costly to manufacture in quantity. In addition, if the membrane develops a slight crack during use or storage, the usefulness of the sensor is lost.

SUMMARY OF THE INVENTION

This invention provides an optical sensor which is relatively easy and inexpensive to manufacture. In addition one or more slight cracks in the membrane will not destroy the usefulness of the sensor.

This can be advantageously accomplished by providing an optical sensor which utilizes a matrix of hydrophobic material and a plurality of particles of hydrophilic material dispersed in the matrix. At least some of the particles carry an optical indicator. The matrix is capable of transmitting light at least at selected wavelengths from outside the matrix to the particles.

With this construction, a slight crack in the matrix may expose and render ineffective the indicator carried by a relatively small number of the particles. However, because it is preferred to utilize a large number of the particles, this would have only a negligible effect on the output signal from the sensor. In addition, it is relatively easy to attach the indicator to the particles and to disperse the particles in the matrix. Also, only a minimum number of components is required.

An optical sensor of this type can be used for various purposes, including ascertaining the partial pressure of gases, such as blood gases. In this regard, the matrix is permeable to the selected gas of interest. The optical indicator carried by the particles is capable of responding to at least a portion of what permeates the matrix such as the partial pressure of the selected gas. Accordingly, when light at appropriate wavelengths is transmitted through the matrix to the indicator, the indicator can respond to the light to provide an optical signal which is related to the property to be measured, such as the partial pressure of the selected gas. For example, the signal may indicate a particular partial pressure of the selected gas or simply indicate the presence or absence of that gas.

Optical indicators for sensors of this kind are typically used in a liquid phase, and for blood gas sensing, the gases to be sensed are also in a liquid. It is, therefore, necessary for the sensor to separate the optical indicator and the blood or other liquid in which the gas to be sensed is found. To accomplish this, the matrix for a gas sensor should be constructed of hydrophobic material. In addition, to facilitate attachment of the optical indicator to the particles and to further tend to separate the indicator from the external liquid medium, the particles should be hydrophilic.

The matrix, being of a hydrophobic material, is by nature most effective in isolating the indicator carried by the particles from water, such as the water in blood. A hydrophobic material is a material, such as a polymeric substance, which retains a small fraction, i.e., less than 20 percent, of water within its structure and which is not miscible with water. Silicone is one example of a hydrophobic material, and by way of example, the following silicones can be used:

silicone elastomer,
  room temperature vulcanizable silicone rubber,
  heat vulcanizable silicone rubber,
  polydimethylsiloxane and silicone-polycarbonate copolymer.

The matrix is considered substantially impermeable to water in that substantially no water is transmitted through the matrix or into contact with the particles as a result of the normal use of the sensor in measuring the partial pressure of a gas. On the other hand, the matrix may transmit some water if held in contact with water for a long period of time, such as several days.

In addition to transmitting the selected gas and isolating the particles and the indicator from water, the matrix also forms a carrier for the particles. As such, it retains within its structure the particles and the indicator carried by the particles. As explained hereinbelow, the indicator may be in solution and form an aqueous phase within the matrix. In this event, the matrix isolates the aqueous phase carried by the particles from the liquid environment presented by the sample from which the selected gas is obtained.

The matrix can be of any desired configuration. In one form, the matrix is spread into a thin membrane-like layer. Regardless of its configuration, the particles are preferably completely enclosed by the matrix and are not exposed at the surface of the matrix, otherwise the isolation function of the matrix would not be totally obtained. To assure that all of the particles are contained within the matrix, the largest cross-sectional dimension of any of the particles should be less than the thickness of the matrix.

Because the particles are of hydrophilic material, they are adapted to receive and contain an aqueous solution of the optical indicator. A hydrophilic material is a material, such as a polymeric substance, which retains a large fraction, such as greater than 20 percent of water, within its structure, but which does not dissolve in water. Various hydrophilic materials can be used, and by way of example, the particles can be made from glass beads or hydrogels, such as:

polyacrylamide, cross-linked dextran, agarose, and poly(hydroxyalkyl methacrylate).

By using hydrophilic material for the particles, the aqueous indicator solution can be soaked into the particles. This is much simpler than encapsulating the indicator solution within small particles using nanoencapsulation techniques.

Each of the particles has an outer surface and preferably has interior voids opening at the outer surface. At least some of the indicator is carried in the voids of the particles. Preferably, each of the particles which carries the indicator is capable of transmitting light at selected wavelengths so that light can be directed toward the indicator carried by the particles.

To hasten the response of the optical indicator to the selected gas, a catalyst may be doped on the particles. The catalyst may be included within the aqueous phase carried by the particles. For example, carbonic anhydrase may be used as catalyst for a carbon dioxide sensor.

If desired, the indicator and catalyst may be carried by the particles in a dry condition. In this event, it is preferred to rehydrate the indicator and catalyst prior to use, and this can be accomplished by soaking the sensor in water over a long period of time, such as several days. Although the matrix is essentially impermeable to water, preferably the matrix will transfer enough water over a long period of time, e.g., several days, to permit rehydration of the indicator.

To obtain repeatable results from sensor to sensor, it is preferred to evenly distribute the particles throughout the matrix. Although the density of the particles can be varied widely, too great a particle density may cause the particles to clump or stick together. Conversely, too low a density of the particles will provide a signal that is too low. By way of example and not by way of limitation, one-to-two parts of particles with the indicator may be used to four parts by weight of the matrix.

The gas to which the sensor responds is a function of the kind of indicator employed, and the gas which the matrix transmits to the indicator. Typical examples of gas, the partial pressures of which can be determined, are carbon dioxide and oxygen, and this invention is particularly adapted to be embodied in a carbon dioxide sensor. Different sensors may be provided for each gas, or if desired, a single sensor can be used. In this latter event, the matrix must transmit all gases which are to be detected, and a first group of the particles would carry an indicator responsive to one gas and a second group of particles would carry an indicator responsive to a second gas. The two indicators provide output signals at different wavelengths so that the signals can be readily distinguished.

The optical indicator may be of various different kinds, and may be, for example, a fluorescent, absorption, luminescent or phosphorescent indicator. Of this group, fluorescent and absorption are presently more practical, and fluorescent indicators are preferred. For example, if it is desired to use fluorescence, pyrenebutyric acid can be used in an oxygen sensor and $\beta$-methylumbelliferone with a sodium bicarbonate buffer in water can be used for a carbon dioxide sensor. As a further example, if light absorption is to be used for a carbon dioxide sensor, phenol red with a sodium bicarbonate buffer in water can be used, and hemoglobin is a suitable absorption indicator for oxygen.

The invention, together with additional features and advantages thereof, may best be understood by reference to the following description taken in connection with the accompanying illustrative drawing.

BRIEF DESCRIPTION OF THE DRAWING

FIG. 1 is a perspective view of an optical sensor constructed in accordance with the teachings of this invention.

FIG. 2 is an enlarged fragmentary sectional view taken generally along line 2—2 of FIG. 1.

FIG. 3 is an enlarged fragmentary sectional view illustrating one of the particles and the surrounding matrix.

FIG. 4 is a schematic view partially in section showing an apparatus for measuring various parameters of a blood sample.

DESCRIPTION OF THE PREFERRED EMBODIMENT

FIG. 1 shows an optical sensor 11 which comprises a matrix 13 (FIG. 2) of hydrophobic material and numerous particles 15 evenly dispersed throughout the matrix. Although the matrix can be of various sizes and configurations, in the form shown in FIGS. 1-3, the matrix is in the form of a thin, cylindrical membrane which may have, for example, a diameter of about 3 millimeters and a thickness of about 100 microns. The matrix 13 has relatively broad circular faces 17 and 19 and a peripheral surface 21.

The sensor 11 is a carbon dioxide gas sensor, and the hydrophobic material of the matrix 13 is permeable to carbon dioxide and essentially impermeable to water. Although various hydrophobic materials having this characteristic and capable of appropriately confining the particles 15 can be employed, in this embodiment, silicone is used.

The particles 15 are completely enclosed within the matrix 13 and are not exposed at the faces 17 and 19 or the peripheral surface 21. The largest cross-sectional dimension of any of the particles 15 should be less than the thickness of the matrix 13. For example, the maximum thickness of each of the particles 15 may be about ⅓ or less the thickness of the matrix 13. For example, the maximum cross-sectional dimension of the particles may be, about 35 microns if the thickness of the matrix is about 100 microns.

The particles 15 are constructed of a hydrophilic material and must be capable of carrying an aqueous phase. For example, the aqueous phase can be either absorbed or adsorbed by the particles 15. Of course, the particles 15 cannot be soluble in the material of the matrix 13. A preferred material for the particles 15 is polyacrylamide.

As best seen in FIG. 3, each of the particles 15 has an outer surface 23 and interior voids 25 opening at the outer surface 23. An indicator 27 is carried in the voids 25. Because the particles 15 are hydrophilic and the matrix 13 is hydrophobic, the indicator 27, which is in an aqueous phase, tends to be retained within the voids 25 and/or on the outer surfaces 23 of the particles 15.

Particles 15 of the type described above are commercially available. For example, polyacrylamide and agarose particles of the type described above are available from Bio-Rad of Richmond, Calif. as Bio-Gel P and Bio-Gel A, respectively, and cross-linked dextran beads are available from Pharmacia of Piscataway, N.J., as Sephadex. Such beads are generally spherical and may be obtained in various sizes.

In the form shown in FIGS. 1-3, the particles 15 are evenly dispersed throughout the matrix 13. Although other ratios can be used, in the illustrated embodiment, one to two parts of the particles 15 with the indicator 27 therein is provided to four parts by weight of the matrix 13.

The indicator 27 is an optical indicator and may be, for example, of the fluorescent or absorption type. The indicator 27 is selected to be responsive to light at least at selected wavelengths and the particular condition which is to be sensed by the sensor 11. In order that the light at the selected wavelengths can be incident upon the indicator 27, the matrix 13 and the particles 15 should both be capable of transmitting light at such selected wavelengths.

In the illustrated embodiment, the indicator 27 is a fluorescent indicator for carbon dioxide, such as $\beta$-methylumbelliferone with a sodium bicarbonate buffer in water. As is well known, carbon dioxide changes the pH of the indicator and the indicator has a fluorescent intensity which is a function of pH.

To hasten the response of the optical indicator 27 to carbon dioxide, a catalyst may be included in the indicator 27. Use of such a catalyst is optional.

The principles described above for making a carbon dioxide sensor can be applied to the construction of a sensor for various other gases and properties. For example, the sensor 11 may be an oxygen sensor by utilizing a hydrophobic material for the matrix 13 which is selectively permeable to oxygen and a material, such as silicone may be used. In addition, the indicator 27 must be one which responds, not only to light, but also to oxygen.

FIG. 4 shows, by way of example, one way that the sensor 11 can be used. The sensor 11 is suitably mounted on a cassette 29. In the embodiment illustrated, the cassette 29 is constructed of a transparent plastic material and comprises an end wall 31 and a peripheral wall 33 defining a hollow interior 35. The end wall 31 has recesses 37 and 39 in its outer and inner surfaces, respectively, with each of the recesses 37 being aligned with one of the recesses 39. The sensor 11 is suitably mounted, such as by an interference fit in one of the recesses 37. Similarly, an optical sensor 11a is mounted in the other recess 37. Of course, additional sensors and rececesses 37 can be provided, if desired. The sensors 11 and 11a sense and measure carbon dioxide and oxygen, respectively.

Fiberoptic bundles 41 and 41a have their end portions received, respectively, within the recesses 39 as shown in FIG. 4. The bundles 41 may be retained in position by a suitable potting compound 43.

Each of the fiberoptic bundles 41 includes one or more optical fibers, and in the embodiment illustrated, each of the bundles includes a plurality of lightsupplying fibers 45 leading from a light source 47 to the end wall 31 and a plurality of return fibers 49 leading from the end wall 31 to optical detectors 51, one of which may be provided for each of the sensors 11 and 11a.

In use, a sample of a substance to be tested, such as blood, is placed into contact with the sensors 11 and 11a or permitted to flow past the sensors in an extracorporeal loop or otherwise. The light source 47 transmits light at selected wavelengths to each of the sensors 11 and 11a. The silicone matrices 13 of the sensors 11 and 11a permit carbon dioxide and oxygen from the blood sample to pass through the matrices into contact with the indicator 27 carried by the particles 15. The light from the light source 47 is transmitted through the end wall 31 and the matrix 13 to the indicator 27 in the particles 15. The indicator 27, being a fluorescent indicator, provides an output optical signal of wavelengths different than the wavelengths transmitted to it from the light source 47. This output signal decreases as the partial pressure of carbon dioxide increases. This output signal is transmitted through the optical fibers 49 to the detectors 51 where the optical signal is processed to provide a reading or other indication of the partial pressure of carbon dioxide in the sample. Appropriate filters may be provided between the detectors 51 and the optical fibers 49 to filter out wavelengths other than those of interest for the particular output signal.

The oxygen sensor 11a may function in the same manner as described above for the carbon dioxide sensor 11.

The sensor 11 can be made, for example, by soaking the particles 15 in an indicator solution to saturate the particles with the indicator solution. The indicator need not be dissolved in the solution as it may be in the solution in the form of a suspension. After the particles 15 are saturated, they are air dried to dry their outer surfaces 23 but to leave the interior of the particles saturated. Alternatively, the particles could be dried throughout and subsequently hydrated.

The particles are then blended with a silicone prepolymer. In this step, the beads are stirred into the silicone to give a homogeneous blend. The blend is then formed into the desired shape, such as a thin membrane using a doctor blade or other suitable apparatus, and the resulting structure is then polymerized.

Although an exemplary embodiment of the invention has been shown and described, many changes, modifications and substitutions may be made by one having ordinary skill in the art without necessarily departing from the spirit and scope of this invention.

I claim:

1. An optical sensor comprising:
   a matrix of hydrophobic material, said matrix being permeable to at least a selected gas in a liquid and substantially impermeable to the liquid;
   a plurality of particles of hydrophilic material dispersed in said matrix, at least some of said particles carrying an optical indicator in solution which is capable of responding to said selected gas; and
   said matrix being capable of transmitting light at least at selected wavelengths from outside said matrix to said particle, and said matrix isolating the particles from the liquid so that the optical indicator can respond to said light and provide an optical signal related to partial pressure of said selected gas.

2. An optical sensor as defined in claim 1 wherein each of said particles which carries said indicator has an outer surface and interior voids opening at said outer surface, and at least some of said indicator is carried in said voids of said particles, said particles which carry said indicator are capable of transmitting light at said selected wavelengths.

3. An optical sensor as defined in claim 1 wherein substantially all of said particles are completely enclosed within said matrix and are not exposed at the surface of said matrix.

4. An optical sensor as defined in claim 1 wherein said hydrophilic material is polyacrylamide.

5. An optical sensor as defined in claim 1 wherein said matrix is arranged in a thin membrane-like layer.

6. An optical sensor as defined in claim 1 wherein said hydrophobic material is silicone.

7. An optical sensor as defined in claim 1 wherein said particles which carry the indicator are substantially spherical.

8. An optical sensor as defined in claim 1 wherein the largest cross-sectional dimension of any of said particles is less than the thickness of said matrix.

9. An optical sensor as defined in claim 1 wherein said particles are substantially evenly dispersed throughout said matrix.

10. An optical sensor as defined in claim 1 wherein said selected gas is carbon dioxide and said matrix is also permeable to oxygen and the optical indicator carried by a first group of said particles is capable of responding to carbon dioxide and the optical indicator carried by a second group of said particles is capable of responding to oxygen whereby the optical sensor responds to both oxygen and carbon dioxide.

11. An optical sensor as defined in claim 1 wherein said matrix is constructed of silicone, said particles are constructed of polyacrylamide, said optical indicator is a fluorescent optical indicator, and said matrix and said particles are arranged in a thin membrane-like layer.

12. An optical sensor as defined in claim 1 wherein said solution is an aqueous solution.

13. An optical sensor as defined in claim 12 wherein said aqueous solution includes a catalyst to hasten the response of the optical indicator to said selected gas.

14. An optical sensor comprising:
a selectively permeable matrix of hydrophobic material, said matrix being permeable to at least a selected gas and substantially impermeable to water;
a plurality of particles of hydrophilic material dispersed in said matrix, at least some of hydrophilic particles carrying an optical fluorescent indicator in solution, said indicator being capable of responding to the selected gas that permeates the matrix substantially all of said particles being completely enclosed by said matrix; and
said matrix being capable of transmitting light at least at selected wavelengths whereby the fluorescent indicator can provide a fluorescent optical signal related to a characteristic of the selected gas and the optical signal can be transmitted out of the matrix.

15. An optical sensor as defined in claim 14 wherein said hydrophilic material is selected from the group consisting of polyacrylamide, cross-linked dextran, agarose, poly(hydroxyalkyl methacrylate), and porous glass.

16. An optical sensor as defined in claim 14 wherein each of said particles which carries said indicator has an outer surface and interior voids opening at said outer surface, and at least some of said indicator is carried in said voids of said particles.

17. An optical sensor as defined in claim 16 wherein said hydrophobic material is silicone.

18. An optical sensor as defined in claim 17 wherein said solution is an aqueous solution.

19. An optical sensor as defined in claim 18 wherein said particles are substantially evenly dispersed throughout said matrix.

20. An apparatus for measuring the partial pressure of at least one gas within a liquid, said apparatus comprising:
a membrane of hydrophobic material, said membrane being permeable to at least one gas and substantially impermeable to a liquid, said membrane being adapted to be positioned in contact with said liquid;
a plurality of hydrophilic particles dispersed in said membrane, at least some of said particles carrying an optical indicator in solution which is capable of responding to said at least one gas, said matrix isolating the particles from the liquid;
means for directing light toward said membrane;
said membrane being capable of transmitting at least some of such light to said particles whereby the optical indicator can respond to said light and provide an optical signal related to partial pressure of said at least one gas; and
means for transmitting said optical signal away from said membrane.

21. An apparatus as defined in claim 20 including a wall with a recess therein, said membrane being in said recess, and said wall being capable of transmitting at least some of the light from the directing means to the membrane.

* * * * *

UNITED STATES PATENT OFFICE
CERTIFICATE OF CORRECTION

Patent No. 4,557,900　　　　　　　　　Dated　December 10, 1985

Inventor(s) Harold A. Heitzmann

It is certified that error appears in the above-identified patent and that said Letters Patent are hereby corrected as shown below:

Change inventorship to read -- Harold A. Heitzmann and Herbert Kroneis -- .

Column 6, line 52, change "particle" to -- particles -- .

Column 7, line 37, after "some of" insert -- said -- .

Signed and Sealed this

Twenty-second Day of July 1986

[SEAL]

Attest:

DONALD J. QUIGG

Attesting Officer　　　Commissioner of Patents and Trademarks